(12) United States Patent
Looijer

(10) Patent No.: US 6,707,296 B2
(45) Date of Patent: Mar. 16, 2004

(54) METHOD FOR DETECTING CRACKS IN ELECTRICALLY CONDUCTING MATERIAL

(75) Inventor: Mark Theodoor Looijer, Amsterdam (NL)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 09/931,982

(22) Filed: Aug. 18, 2001

(65) Prior Publication Data

US 2002/0047706 A1 Apr. 25, 2002

(30) Foreign Application Priority Data

Aug. 24, 2000 (EP) .............................. 00307301

(51) Int. Cl.[7] .......................... G01N 27/82; G01B 5/28
(52) U.S. Cl. ......................................... 324/240; 702/38
(58) Field of Search ................................. 324/240, 237, 324/242, 263, 207.16, 230, 220, 238, 225; 702/35, 38

(56) References Cited

U.S. PATENT DOCUMENTS

| 4,821,204 A | * | 4/1989 | Huschelrath ............... 324/240 |
| 4,839,593 A | * | 6/1989 | Spies ......................... 324/240 |
| 4,929,896 A | * | 5/1990 | Lara ........................... 324/240 |
| 4,929,898 A | * | 5/1990 | Spies ......................... 324/242 |
| 4,990,851 A | * | 2/1991 | Spies ......................... 324/240 |
| 5,028,100 A | * | 7/1991 | Valleau et al. .............. 324/238 |
| 5,416,411 A |   | 5/1995 | Elsmore ..................... 324/230 |
| 5,461,313 A | * | 10/1995 | Bohon et al. ............... 324/240 |
| 6,037,768 A |   | 3/2000 | Moulder et al. |
| 6,291,992 B1 | * | 9/2001 | van Andel et al. .......... 324/240 |
| 6,538,435 B2 | * | 3/2003 | Crouzen et al. ............ 324/232 |
| 6,570,379 B2 | * | 5/2003 | Crouzen et al. ............ 324/240 |

FOREIGN PATENT DOCUMENTS

| JP | 11-101783 | 4/1999 |
| WO | 95/00840 | 1/1995 |
| WO | 98/02714 | 1/1998 |

OTHER PUBLICATIONS

"Nondestructive Evaluation for Bridge Management in the Next Century", Chase et al., U.S. Department of Transportation Federal Highway Administration, vol. 61, No. 1, Jul./Aug. 1997.*
PCT International Search Report dated Jul. 25, 2002.
Foreign Search Report dated Feb. 27, 2001.

* cited by examiner

Primary Examiner—John Barlow
Assistant Examiner—Toan M Le

(57) ABSTRACT

Method of detecting cracks in an object of an electrically conducting material that is covered by a non-conductive layer using a probe comprising a transmitter coil for inducing eddy currents in the object and a receiver coil comprising selecting a set of points of the object which are to be inspected; and which method further comprises for each point positioning the probe at the point, activating the transmitter coil to induce eddy currents in the object; creating a record of the signal provided by the receiver coil over a period of time; and examining the record and comparing it to reference records, wherein the presence or absence of a crack can be inferred from the comparison.

3 Claims, 1 Drawing Sheet

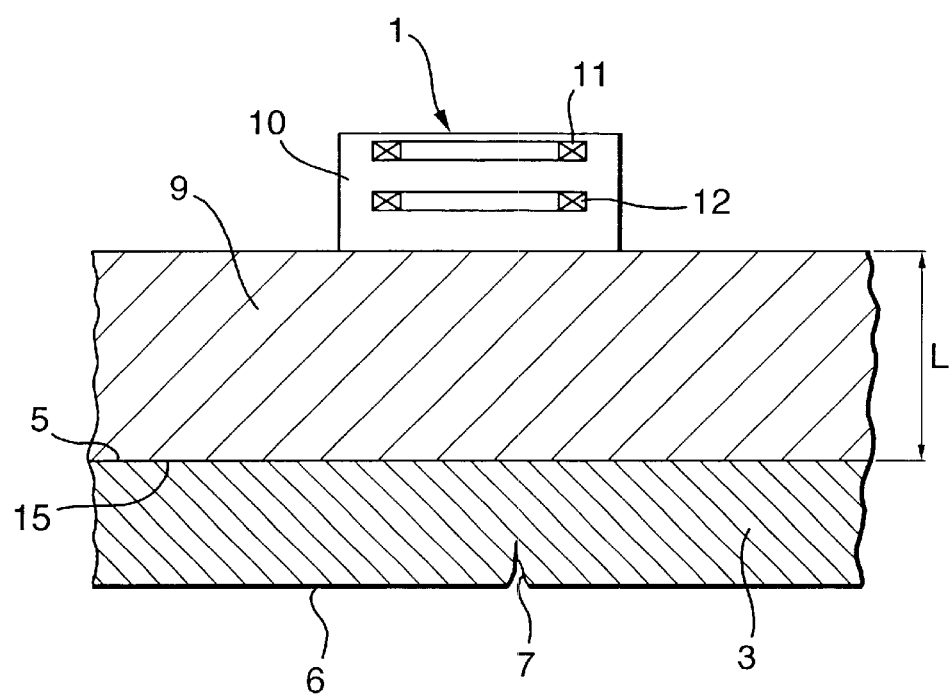

METHOD FOR DETECTING CRACKS IN ELECTRICALLY CONDUCTING MATERIAL

This application claims the benefit of Application No. 00307301.2 filed on Aug. 24, 2000 under 35 U.S.C. §119, §365(a), or §365(b). (For originals)

BACKGROUND OF THE INVENTION

1. Field of the Invention

The present invention relates to detecting the presence of a crack in an object of electrically conducting material by means of eddy currents induced in the object. The object can be a plate, such as a support plate or a shell, such as a wall. The electrically conducting material can be carbon steel or stainless steel. More in particular, the present invention relates to detecting cracks in an object of electrically conducting material that is covered by a relatively thick layer of a non-conductive material.

2. Description of Related Art

International patent application publication No. 95/00 840 discloses a method of detecting cracks in an object of electrically conducting material. The known method comprises inducing an eddy current into a portion of the object with an abruptly changing magnetic field; while the induced eddy current decays in the object portion, detecting the decay of the induced eddy current; determining with respect to time the derivative of the decay of the induced eddy current; determining a value from the derivative which is representative of the thickness of the portion; determining, by use of a magnetic flux leakage method, the wall thickness of the object portion; and inferring that a plurality of cracks is present where a reduction in wall thickness is indicated by the derivative of the decay and no reduction in wall thickness is indicated with the magnetic flux method.

Thus in the known method, two different methods are required to determine the presence of a crack: an eddy-current method and a magnetic flux leakage method. However, the magnetic flux leakage method can only be applied to relatively small lift-offs, in practice only up to 10 mm. Because the steel needs to be magnetized, the magnetic flux leakage method becomes impractical and insensitive for larger lift-offs. Furthermore, a magnetic flux leakage method requires a bulky inspection apparatus that consumes much electrical power. This is a drawback for the inspection of bridges, since the inspection tools need to be portable and battery operated.

SUMMARY OF THE INVENTION

It is an object of the present invention to provide a method of detecting cracks in an object of electrically conducting material wherein only one inspection method is used.

To this end the present invention provides a method of detecting cracks in object of an electrically conducting material that is covered by a non-conductive layer using a probe comprising a transmitter system for inducing eddy currents in the object, and a receiver system for providing a signal indicative of the strength of a magnetic field or changes in the strength of a magnetic field, which method comprises:

a) selecting a set of points of the object which are to be inspected;
b) selecting a first inspection point from the set;
c) positioning the probe at the selected inspection point, activating the transmitter system to induce eddy currents in the object;
d) creating a record of the signal provided by the receiver system over a period of time;
e) examining the record and comparing it to reference records, wherein the presence or absence of a crack can be inferred from the comparison; and
f) selecting a next point of the set and repeating steps c) through e) until all points have had their turn.

In the specification and in the claims, the term 'non-conductive layer' is used to refer to a layer of material that has a conductivity that is much lower than the conductivity of the object.

BRIEF DESCRIPTION OF THE DRAWINGS

The invention will now be described by way of example in more detail with reference to the drawing, which shows schematically a vertical section of a probe and an object of electrically conducting material.

DESCRIPTION OF THE PREFERRED EMBODIMENTS

A probe 1 is arranged near an object of electrically conducting material in the form of a flat plate 3. The object 3 of electrically conducting material has a near surface 5 (nearest to the probe 1) and a far surface 6. The plate 3 has a crack 7 that extends in a direction perpendicular to the plane of drawing at the far surface 6. The object is covered by a layer 9 of non-conductive material.

The probe 1 comprises a box 10. The box 10 includes a transmitter system comprising a transmitter coil 11 and a receiver system comprising receiver 12. The diameter of the transmitter coil 11 is substantially equal to the thickness of the layer 9 of non-conductive material. The receiver coil 12 has a diameter that is substantially equal to the diameter of the transmitter 11. Here, as in the claims, substantially equal means within ±10%.

The transmitter system includes a device (not shown) for energizing the transmitter coil 11, and the receiver system includes a device (not shown) for recording the signals from the receiver coil 12.

During normal operation, a set of points is selected on the near surface 5 of the object 3, at which points an inspection is to be carried out. In the FIGURE, one of the points is referred to with reference numeral 15.

The probe 1 is positioned at the selected inspection point 15. The distance L between the probe and the near surface 5 of the object is the lift-off, which lift-off is approximately equal to the thickness of the layer 9 of non-conductive material.

Then the transmitter system is activated by allowing currents to flow through the transmitter coil 11. Then eddy currents are induced in the object 3 by abruptly de-energizing the transmitter coil 11.

The eddy currents induced in the plate 3 generate an electromagnetic field, and a record of the signal provided by the receiver coil 12 over a period of time is created. The record is examined and compared with a reference record, wherein the presence or absence of a crack can be inferred from the comparison. Then a next inspection point is selected and so on.

A first way in which the comparison can be carried out is by comparing the critical times. The critical time is the time it takes for the eddy currents that diffuse through the plate 3 to reach the far surface 6.

Another way in which the comparison can be carried out is by comparing the decay of the received signal over a period of time with a reference decay indicative of a known wall thickness.

In the probe as described with reference to the drawing, the probe includes a single transmitter coil and a single receiver coil. However, both the transmitter and the receiver can comprise two spaced apart coils. The transmitter coils have a diameter that is substantially equal to the thickness of the layer of non-conductive material, and their lateral spacing is at most equal to the diameter of the coils, and suitably between 10 and 90% of the diameter. And the receiver coils have a diameter that is substantially equal to the diameters of the transmitter coils, the diameter ratio being in the range of from 50 to 90%, and their lateral spacing is at most equal to the diameter of the coils, and suitably between 10 and 90% of the diameter.

The method according to the invention is particularly suitable where the object is a steel plate. For example a support plate of a bridge. Such a support plate is covered with a layer of asphalt or a layer of concrete. When concrete is used, it can be reinforced concrete. Like concrete, reinforced concrete has a very low conductivity compared with the steel support plate, so that it can be regarded as non-conductive material. Such layers of non-conductive material can have a thickness of up to about 80 mm.

It is well known that the eddy current technique used in the present invention can be used to determine the thickness of a plate, and in particular to determine local variation in the thickness of the plate as caused by corrosion. Such local variations can as well be detected when the plate is covered by a layer of insulation, so that the probe is not in direct contact with the plate. Applicant has found that the possibility of detecting local variations in the thickness decreases with increasing lift-off, and for a lift-off larger than about 20 mm local variations in thickness are nearly impossible to detect with the eddy-current method. A crack, however, is a defect that causes a considerable response because eddy currents generated in the plate cannot go through the crack. Thus cracks at such a larger lift-off can still be detected. Therefore the present invention is particularly suitable for detection of cracks in a plate under a relatively thick layer of nonconductive material.

Moreover, because bridges are used in adverse environments, the steel parts are well protected against corroding agents, so that a difference that surfaces in the comparison is caused by a crack. Thus the present invention provides a simple way of detecting cracks in the steel support plates of bridges.

What is claimed is:

1. A method of detecting cracks in an object of steel, such as a support plate of a bridge, which object is covered by a non-conductive layer of asphalt, concrete, or reinforced concrete, which layer has a thickness larger than 20 mm, using a probe comprising a transmitter system for inducing eddy currents in the object, and a receiver system for providing a signal indicative of the strength of a magnetic field or changes in the strength of a magnetic field, which method comprises a) selecting a set of points of the object which are to be inspected;
   b) selecting a first inspection point from the set;
   c) positioning the probe at the selected inspection point, activating the transmitter system to induce eddy currents in the object;
   d) creating a record of the signal provided by the receiver system over a period of time;
   e) examining the record and comparing it to reference records, wherein the presence or absence of a crack can be inferred from the comparison; and
   f) selecting a next point of the set and repeating steps c) through e) until all points have had their turn.

2. The method according to claim 1, wherein the transmitter system includes a transmitter coil having a diameter that is substantially equal to the thickness of the non-conductive layer.

3. The method according to claim 2, wherein the receiver system includes a receiver coil having a diameter that is substantially equal to the diameter of the transmitter coil.

* * * * *